United States Patent [19]
Guo et al.

[11] Patent Number: 5,905,175
[45] Date of Patent: May 18, 1999

[54] SYNTHESIS AND PURIFICATION OF 3,3-DIMETHYLBUTYRALDEHYDE VIA OXIDATION OF 1-CHLORO-3,3-DIMETHYLBUTANE WITH DIMETHYL SULFOXIDE

[75] Inventors: Zhi Guo, Chicago; Indra Prakash, Hoffman Estates, both of Ill.

[73] Assignee: The NutraSweet Company, Chicago, Ill.

[21] Appl. No.: 09/081,609

[22] Filed: May 20, 1998

[51] Int. Cl.$^6$ .................................................. C07C 45/63
[52] U.S. Cl. ........................... 568/490; 568/449; 568/450
[58] Field of Search .................................. 568/450, 427, 568/426, 449, 490

[56] References Cited

U.S. PATENT DOCUMENTS

| | | | |
|---|---|---|---|
| 4,175,204 | 11/1979 | Babler | 560/262 |
| 5,480,668 | 1/1996 | Nofre | 426/548 |
| 5,510,508 | 4/1996 | Claude | 560/41 |

FOREIGN PATENT DOCUMENTS

| | | |
|---|---|---|
| 0 374 952 | 6/1990 | European Pat. Off. . |
| 0 391 652 | 10/1990 | European Pat. Off. . |

OTHER PUBLICATIONS

Paritosh et al, Synthetic Commun., 16(11), 1343–1346, 1986.
Perrin & Perrin, Purification of Laboratory Chemicals, pp. 67–68, 1986.
Acta,Chem.Scand., vol. 13, p. 612, 1959.
N. Kornblum, "A New and Selective Method of Oxidation", J. Am. Chem. Soc., vol. 81, No. 15, pp. 4113–4114 (1959).
H. Nace, "Reactions of Sulfoxides with Organic Halides", J. Org. Chem., vol. 24, No. 11, pp. 1792–1793 (1959).
N. Kornblum, "A New and Selective Method of Oxidation", J. Am. Chem. Soc., vol. 79, No. 24, p. 6562 (1957).
R. Major, "Reactions of Organic Halides with Dimethyl Sulfoxide", J. Org. Chem., vol. 23, No. 10, pp. 1563–1564 (1958).
P. Dave, "An Improved Direct Oxidation of Alkyl Halides to Aldehydes", Syn. Comm., vol. 16, No. 11, pp. 1343–1346 (1986).
B. Ganem, "Silver–Assisted Dimethylsulfoxide Oxidations"; Tetra. Lett., No. 11, pp. 917–920 (1974).
C. Cheung, "Effect of Pressure on the Rate of Methylation of a Buttressed Pyridine", J. Org. Chem., vol. 54, No. 3, pp. 570–573 (1989).
N. Wilson, "A Desilylation and a One–Pot Desilylation–Oxidation of Aliphatic ter–Butyldimethylsilyl Ethers . . . " J. Org. Chem., vol. 61, No. 9, pp. 2918–2919 (1996).
K. Wiberg, "Thermochemical Studies of Carbonyl Reactions", J. Am. Chem. Soc., vol. 103, No. 13, pp. 4473–4478 (1981).
T. Fujii, "Synthesis of 3–tert–Butylpyridine", Chem. and Pharm. Bull., vol. 26, No. 10, pp. 3233–3237 (1978).
H. Mager, "Activation and Transfer of Oxygen–IX", Tetrahedron, vol. 30, pp. 917–927 (1974).

*Primary Examiner*—Gary Geist
*Assistant Examiner*—Sreeni Padmanabhan
*Attorney, Agent, or Firm*—Fitzpatrick, Cella, Harper & Scinto

[57] ABSTRACT

1-chloro-3,3-dimethylbutane is oxidized by dimethyl sulfoxide, in the presence of an effective amount of inorganic bromide or iodide, and in the present of an effective amount of base, to produce 3,3-dimethylbutyraldehyde.

18 Claims, No Drawings

5,905,175

SYNTHESIS AND PURIFICATION OF 3,3-DIMETHYLBUTYRALDEHYDE VIA OXIDATION OF 1-CHLORO-3,3-DIMETHYLBUTANE WITH DIMETHYL SULFOXIDE

BACKGROUND OF THE INVENTION

1. Field of the Invention

This invention is directed to the synthesis and purification of 3,3-dimethylbutyraldehyde. In particular, the present invention is related to the oxidation of 1-chloro-3,3-dimethylbutane with dimethyl sulfoxide (DMSO) to form 3,3-dimethylbutyraldehyde followed by the purification of the crude product.

2. Related Background Art

1-Chloro-3,3-dimethylbutane can be synthesized by treating tert-butyl chloride and ethylene with aluminum trichloride as reported in Acta Chem. Scand., Vol. 13 (1959), page 612, the disclosure of which is incorporated herein by reference. The oxidation of benzyl halides by dimethyl sulfoxide into benzyl aldehydes was reported in Journal American of Chemical Society, Vol. 81 (1959), pages 4113–4114, and Journal of Organic Chemistry, Vol. 24 (1959), pages 1792–1793. The oxidation of primary halides, which are activated by an adjacent carbonyl group, by dimethyl sulfoxide into the corresponding aldehydes was reported in Journal of American Chemical Society, Vol. 79 (1957), page 6562, and Journal of Organic Chemistry, Vol. 23 (1958), page 1563.

The oxidation of primary aliphatic chlorides and bromides by dimethyl sulfoxide in the presence of 1.5 equivalent NaI was reported in Synthetic Communications, Vol. 16 (1986), pages 1343–1346. The reaction was reported to yield the corresponding aldehydes in 56–96% yield. This article does not disclose the oxidation of 1-chloro-3,3-dimethylbutane and does not suggest that a catalytic amount of iodide is effective for the oxidation. Journal of American Chemical Society, Vol. 81 (1959), page 4113–4114, and Tetrahedron Letter (1974), page 917–920 disclose that simple primary chlorides and bromides can be converted to tosylates or tetrafluoroborates followed by oxidation with dimethyl sulfoxide to generate aldehydes.

U.S. Pat. No. 4,175,204 describes the use of sodium bromide with activated allyl chloride. A substituted allyl chloride was oxidized to its corresponding aldehyde with DMSO in the presence of catalytic amounts of sodium bromide.

3,3-Dimethylbutyraldehyde is an intermediate that is useful in the preparation of the sweetener N-[N-(3,3-dimethylbutyl)-L-α-aspartyl]-L-phenylalanine, 1-methyl ester, disclosed in U.S. Pat. No. 5,480,668 and U.S. Pat. No. 5,510,508. Commercially available 3,3-dimethylbutyraldehyde is currently prepared using methods that are very costly and that result in a product that is not commercially practicable.

Several methods are known for the preparation of 3,3-dimethylbutyraldehyde by the oxidation of 3,3-dimethyl butanol, as described in EP 0391652; EP 0374952; Journal of Organic Chemistry, Vol. 54, p. 570 (1989); Journal of Organic Chemistry, Vol. 61, p. 2918 (1996); and Journal of the American Chemical Society, Vol. 103, p. 4473 (1981). There is no method reported, however, that prepares 3,3-dimethylbutyraldehyde by the oxidation of 1-chloro-3,3-dimethylbutane.

Furthermore, the crude product from the oxidation of 1-chloro-3,3-dimethylbutane with DMSO typically contains dimethyl disulfide and dimethyl sulfide, besides other sulfur and non-sulfur containing impurities. Conventional distillation would not be able to separate dimethyl disulfide (boiling point 109° C.) from 3,3-dimethylbutyraldehyde (boiling point 104–106° C.) because their boiling points are very close. Contamination by even trace amounts of an organic sulfur impurities in 3,3-dimethylbutyraldehyde is highly undesirable for its use in the synthesis of N-[N-(3,3-dimethyl)-L-α-aspartyl]-L-phenylalanine, 1-methyl ester, which is typically produced by the hydrogenation of a mixture of 3,3-dimethylbutyraldehyde and aspartame in the presence of a precious metal catalyst. It is well known that such catalysts can be deactivated by organic sulfur compounds. Thus, any organic sulfur impurity in 3,3-dimethylbutyraldehyde must be removed before its hydrogenation with aspartame. Accordingly, it is highly desired to develop a purification procedure which can remove all impurities, including sulfur-containing compounds, in the crude 3,3-dimethylbutyraldehyde products.

Purification of aldehydes by their conversion into a solid aldehyde/bisulfite adduct has been described in the literature. "Purification of Laboratory Chemicals" (Pergamon Press, 1988) pages 60–61 is incorporated by reference herein as general reference for this methodology.

Chemical Pharmaceutical Bulletin Vol, 26 (1978) pages 3233–3236, incorporated by reference herein, discloses a method of purifying 3,3-dimethylbutyraldehyde, which was synthesized from the reaction of the neo-hexyl magnesium bromide with orthoformate, by its conversion into a 3,3-dimethylbutyraldehyde/sodium bisulfite adduct, followed by aldehyde regeneration with aqueous sodium bicarbonate. This purification involved the following steps: stirring a mixture of the isolated crude product and aqueous sodium bisulfite solution at room temperature overnight; isolating the solid 3,3-dimethylbutyraldehyde/sodium bisulfite adduct by filtration; washing the isolated solid adduct and the aqueous filtrate with ether; combining the washed isolated solid adduct with the aqueous filtrate and sodium bicarbonate to form a mixture; and steam-distilling the mixture. Further manipulation gave the purified 3,3-dimethylbutyraldehyde. However, this procedure was not designed for the removal of trace amounts of organic sulfur compounds from the aldehyde and can not give 3,3-dimethylbutyraldehyde that is free of organic sulfur contamination as required for the synthesis of N-(N(3,3-dimethyl)-L-α-aspartyl)-L-phenylalanine, 1-methyl ester.

Accordingly, a method for preparing 3,3dimethylbutyraldehyde which is both economical and of greater purity is highly desired.

SUMMARY OF THE INVENTION

This invention is directed to a method of preparing 3,3-dimethylbutyraldehyde by contacting 1-chloro-3,3-dimethylbutane and dimethyl sulfoxide, in the presence of an effective amount of inorganic bromide or iodide, and in the presence of an effective amount of base, followed by purification via an aldehyde bisulfite adduct, to produce 3,3-dimethylbutyraldehyde. An organic compound, including 1-chloro-3,3-dimethylbutane, may be used as a solvent in the reaction.

The invention is also directed to a method to produce 3,3-dimethylbutyraldehyde by contacting tert-butyl chloride and ethylene, in the presence of aluminum trichloride, effective to produce 1-chloro-3,3-dimethylbutane, isolating the produced 1-chloro-3,3-dimethylbutane, and contacting the isolated 1-chloro-3,3-dimethylbutane with dimethyl sulfoxide, in the presence of an effective amount of in organic bromide or iodide, and in the presence of an effective amount of base, followed by purification via an aldehyde bisulfite adduct, to produce 3,3-dimethylbutyraldehyde.

The method of this invention allows for the preparation of 3,3-dimethylbutyraldehyde in a reproducible and highly economical manner with greater purity so that use of the aldehyde in the preparation of a sweetener derived from aspartame is commercially practicable.

DETAILED DESCRIPTION OF THE INVENTION

In the present invention, 3,3-dimethylbutyraldehyde is formed by the oxidation of 1-chloro-3,3-dimethylbutane by dimethyl sulfoxide (DMSO) in the presence of an effective amount of inorganic bromide or iodide. An effective amount of a base is needed to facilitate the reaction.

The 1-chloro-3,3-dimethylbutane, DMSO, and halide are typically contacted at a temperature in the range of from about 60° C. to about 200° C., preferably from about 120° C. to about 160° C., and most preferably from about 130° C. to about 150° C.

The 1-chloro-3,3-dimethylbutane and DMSO are typically utilized in the ratio of from about 1:100 by wt. to about 1:1 by wt., preferably from about 1:20 by wt. to about 1:2 by wt., most preferably from about 1:10 by wt. to about 1:3 by wt.

The inorganic bromide or iodide is preferably sodium iodide, potassium iodide, magnesium iodide, zinc iodide, lithium iodide, calcium iodide, aluminum iodide, ammonium iodide, tetraalkyl ammonium iodide, sodium bromide, potassium bromide, magnesium bromide, zinc bromide, lithium bromide, calcium bromide, aluminum bromide, ammonium bromide, tetraalkyl ammonium bromide. The ration of inorganic bromide/1-chloro-3,3-dimethylbutane is typically in the range of 0.05 to about 10 equivalent, preferably, 0.2 to 2 equivalent, and most preferably 0.4 to 1 equivalent. The ratio of inorganic iodide/1-chloro-3,3-dimethylbutane is typically in the range of 0.01 to about 1.5 equivalent, preferably, 0.05 to 0.75 equivalent, and most preferably 0.05 to 0.5 equivalent.

The base is selected from an inorganic or an organic base. A mixture of bases is also effective. An inorganic base is preferably sodium bicarbonate, potassium bicarbonate, sodium carbonate, potassium carbonate, zinc oxide, aluminum oxide, zinc carbonate, magnesium oxide, calcium oxide, calcium carbonate, magnesium carbonate, potassium phosphates (monobasic, dibasic and tribasic), sodium phosphates (monobasic, dibasic and tribasic), ammonium phosphate, calcium phosphate, magnesium phosphate, or ammonia. An organic base is preferably a tertiary amine, a secondary amine, or a pyridine derivative. The ration of base/1-chloro-3,3-dimethylbutane is typically in the range of 1 to about 10 equivalent, preferably, 1 to 5 equivalent, and most preferably 1 to 2 equivalent.

The reaction is allowed to proceed for a period of time from about 30 minutes to about 2880 minutes, preferably from about 180 minutes to about 1440 minutes, most preferably from about 360 minutes to about 840 minutes.

The crude aldehyde was collected and purified via its sodium bisulfite adduct using a water-immiscible solvent. The purification includes the following steps:

A. A mixture of the crude product, a water-immiscible solvent, and an aqueous sodium bisulfite solution was stirred for a period of time.

B. The solid adduct was isolated by filtration and the solid was washed thoroughly with a mixture of an alcohol and a water-immiscible solvent.

C. The solid was dried.

D. 3,3-dimethylbutyraldehyde was regenerated by heating a mixture of the dried solid aldehyde/bisulfite adduct and an aqueous inorganic base or acid, followed by distillation.

The 3,3-dimethylbutyraldehyde produced and purified by the methods of this invention are sufficiently pure for their use in the synthesis of N-[N-(3,3-dimethyl)-L-α-aspartyl]L-phenylalanine, 1-methyl ester. The recovery of 3,3-dimethylbutyraldehyde from the crude mixture was generally higher than 80%. The water-immiscible solvent in Steps A and B is preferably an ether, a hydrocarbon compound, an ester or a mixture of the above. The stirring time in Step A is from about 10 minutes to about 1440 minutes, preferably from about 20 minutes to 600 minutes, most preferably from 30 minutes to 360 minutes. The alcohol in Step B is preferably methyl alcohol, ethyl alcohol, propyl alcohols, butyl alcohols. The inorganic acid or base in Step D is preferably hydrochloric acid, sulfuric acid, phosphoric acid, sodium bicarbonate, sodium carbonate, potassium bicarbonate, potassium carbonate, calcium carbonate. The heating of the mixture in Step D, is to a temperature from about 40° C. to the boiling temperature of the mixture.

The 1-chloro-3,3-dimethylbutane precursor can be formed by any convenient method such as, for example, by the treatment of tert-butyl chloride and ethylene with an acidic catalyst such as aluminum trichloride, iron trichloride, and solid acid. The thus formed 1-chloro-3,3-dimethylbutane is then treated with DMSO in the manner described above to form 3,3-dimethylbutyraldehyde.

The examples which follow are intended to illustrate a preferred embodiment of the present invention, and no limitation of the invention is implied.

EXAMPLE 1

Preparation of 1-Chloro-3,3-Dimethylbutane

A 250 ml 3-necked round bottom flask was equipped with a mechanical agitator, a gas inlet and a gas outlet connected to a bubbler. 57.5 g tert-butyl chloride was charged in the flask and cooled to −20° C. 0.88 g anhydrous aluminum chloride was added and ethylene was introduced. The rate of the reaction was controlled by either adjusting agitation or the gas flow rate and the temperature was maintained at −15 to −20° C. As soon as the gas-uptake ceased (after about 45 minutes), ethylene was removed. The mixture was decanted into 40 ml water. The organic layer was separated to yield the crude product (75 g, 80–85% purity). Fractional distillation at 111–115° C. gave 52.5 g (70%) of the pure the 1-chloro-3,3-dimethylbutane.

EXAMPLE 2

Oxidation of 1-Chloro-3,3-Dimethylbutane with DMSO (Dimethyl Sulfoxide)/NaI

A 100 ml round bottom flask was loaded with 2.0 g 1-chloro-3,3-dimethylbutane, 2.0 g sodium bicarbonate, 1.0 g NaI, and 20 g dimethyl sulfoxide -$d_6$. The flask was flushed with nitrogen and heated to 140° C. for 2.5 hours. $^1$H NMR of the reaction mixture indicated that 62% 1-chloro-3,3-dimethylbutane was converted to 3,3-dimethylbutyraldehyde.

EXAMPLE 3

Oxidation of 1-Chloro-3,3-Dimethylbutane with DMSO/KBr

A 100 ml round bottom flask was loaded with 3.1 g 1-chloro-3,3-dimethylbutane, 2.1 g sodium bicarbonate, 1.5 g KBr, and 18 g dimethyl sulfoxide-$d_6$. The flask was flushed with nitrogen and heated to 145° C. for 4.5 hours. $^1$H NMR of the reaction mixture indicated that the yield of 3,3-dimethylbutyraldehyde was 70%.

EXAMPLE 4

Oxidation of 1-Chloro-3,3-Dimethylbutane with DMSO/NaBr

A 500 ml round button flask fitted with a fractional distillation setup was loaded with 46.1 g 1-chloro-3,3-dimethylbutane, 23 g sodium bromide, 20 g zinc oxide and 276 g dimethyl sulfoxide (DMSO). The mixture was stirred with a magnetic stirrer apparatus and heated with an oil bath to 140–150° C. (pot temperature 135–140° C. under nitrogen for 12–14 hours, during which some low boiling point fractions (mostly dimethyl sulfide) were collected in a receiver flask. House vacuum was applied to the remaining mixture and the crude aldehyde product was collected in a new receiver. The weight of this crude product was 31.6 g (80% 3,3-dimethylbutyraldehyde).

EXAMPLE 5

Purification of Crude 3,3-Dimethylbutyraldehyde

A solution made from 30 g sodium bisulfite in 60 ml water was added dropwise, over a period of 20 minutes with vigorous agitation, to a mixture of (i) 30.6 g of the crude product in Example 4 and (ii) 240 ml methyl tert-butyl ether (MTBE), cooled with an ice water bath. White solids precipitated upon the addition of the sodium bisulfite. The thus formed slurry was stirred for another 80 minutes with continued ice cooling. This stirred cold mixture was filtered and the remaining solid was washed with 100 ml MTBE and 2×100 ml 60/40 (vol/vol) MTBE/methanol. The solid was dried in a house vacuum oven (40° C.) overnight. The weight of the dry solid was 48.0 g.

(i) 40.0 g of the dry solid, (ii) 22 g sodium bicarbonate, and (iii) 200 ml water were loaded to a 250 ml round bottom flask. This mixture was heated to boiling and distilled to yield 18.0 g 3,3-dimethylbutyraldehyde that was sufficiently pure for the synthesis of N-[N-(3,3-dimethyl)-L-α-aspartyl]-L-phenylalanine, 1-methyl ester. The yield was 58%, based on 1-chloro-3,3dimethylbutane.

Other variations and modifications of the present invention will be obvious to those skilled in the art. This invention is not limited except as set forth in the claims.

What is claim is:

1. A method for preparing 3,3-dimethylbutyraldehyde comprising the step of:

contacting 1chloro-3,3-dimethylbutane and dimethyl sulfoxide, in the presence of inorganic bromide in amount in the range of about 0.05 to about 10 equivalents or inorganic iodide in an amount in the range of about 0.01 to about 1.5 equivalents, and in the presence of a base in an amount in the range of about 1 to about 10 equivalents, to produce 3,3-dimethylbutyraldehyde.

2. The method of claim 1, wherein said inorganic bromide or inorganic iodide is sodium iodide, potassium iodide, magnesium iodide, magnesium iodide, zinc iodide lithium iodide, calcium iodide, aluminum iodide, ammonium iodide, tetraalkyl ammonium iodide, sodium bromide, potassium bromide, magnesium bromide, zinc bromide, lithium bromide, calcium bromide, aluminum bromide, ammonium bromide, or tetraalkyl ammonium bromide.

3. The method of claim 1, wherein said base is sodium bicarbonate, potassium bicarbonate, sodium carbonate, potassium carbonate, zinc oxide, zinc carbonate, magnesium oxide, calcium oxide, aluminum oxide, magnesium carbonate, calcium carbonate, monobasic potassium phosphate, dibasic potassium phosphate, tribasic potassium phosphate, monobasic sodium phosphate, dibasic sodium phosphate, tribasic sodium phosphate, ammonium phosphate, calcium phosphate, magnesium phosphate, ammonia, a tertiary amine, a secondary amine, a pyridine derivative, or a mixture thereof.

4. The method of claim 1, 2 or 3, wherein said step of contacting is at a temperature ranging from about 60° C. to about 200° C.

5. The method of claim 1, further including the steps of:

mixing the 3,3-dimethylbutyraldehyde with a first water-immiscible solvent and an aqueous solution of sodium bisulfite to form a bisulfite precipitate of the 3,3-dimethylbutyraldehyde;

washing said bisulfite precipitate with a second water-immiscible solvent or a mixture of an alcohol and said second water-immiscible solvent; and contacting, with heating, said washed bisulfite precipitate with an aqueous inorganic base or an aqueous inorganic acid to yield purified 3,3-dimethylbutyraldehyde.

6. The method of claim 5, further including a step of distilling after the step of contacting, wherein the distillation isolates said purified 3,3-dimethylbutyraldehyde.

7. The method of claim 5, wherein the first water-immiscible solvent is the same as the second water-immiscible solvent.

8. The method of claim 5, wherein the first water immiscible solvent is an ether, a hydrocarbon, an ester, or a mixture of thereof, and the second water-immiscible solvent is an ether, a hydrocarbon, an ester, or a mixture of thereof.

9. The method of claim 5, wherein said aqueous inorganic base or aqueous inorganic acid is an aqueous solution of hydrochloric acid, sulfuric acid, phosphoric acid, sodium bicarbonate, sodium carbonate, potassium bicarbonate, potassium carbonate, or calcium carbonate.

10. A method for preparing 3,3-dimethylbutyraldehyde comprising the steps of (a) contacting tert-butyl chloride and ethylene, in the presence of aluminum trichloride to produce 1-chloro-3,3-dimethylbutane;

(b) isolating said produced 1-chloro-3,3-dimethylbutane; and (c) contacting said isolated 1-chloro-3,3-dimethylbutane with dimethyl sulfoxide in the presence of inorganic bromide in an amount in the range of about 0.05 to about 10 equivalents or inorganic iodide in an amount in the range of about 0.01 to about 1.5 equivalents, and in the presence of a base in an amount in the range of about 1 to about 10 equivalents, to produce 3,3-dimethylbutyraldehyde.

11. The method of claim 10, wherein said inorganic bromide or inorganic iodide is sodium iodide, potassium iodide, magnesium iodide, zinc iodide, lithium iodide, calcium iodide, aluminum iodide, ammonium iodide, tetraalkyl ammonium iodide, sodium bromide, potassium bromide, magnesium bromide, zinc bromide, lithium bromide, calcium bromide, aluminum bromide, ammonium bromide, tetraalkyl ammonium bromide.

12. The method of claim 10, wherein said base is sodium bicarbonate, potassium carbonate, sodium carbonate, potassium carbonate, zinc oxide, zinc carbonate, magnesium oxide, calcium oxide, aluminum oxide, magnesium carbonate, calcium carbonate, monobasic potassium phosphate, dibasic potassium phosphate, tribasic potassium phosphate, monobasic sodium phosphate, dibasic sodium phosphate, tribasic sodium phosphate, ammonium phosphate, calcium phosphate, magnesium phosphate, ammonia, a tertiary amine, a secondary amine, a pyridine derivative, or a mixture there.

13. The method of claim 10, 11 or 12, wherein said step of contacting is at a temperature ranging from about 60° C. to about 200° C.

14. The method of claim 10, further including the steps of:
mixing the 3,3-dimethylbutyraldehyde with a first water-immiscible solvent and an aqueous solution of sodium bisulfite to form a bisulfite precipitate of the 3,3-dimethylbutyraldehyde;

washing said bisulfite precipitate with a second water-immiscible solvent or a mixture of an alcohol and said second water-immiscible solvent; and contacting, with heating, said washed bisulfite precipitate with an aqueous inorganic base or an aqueous inorganic acid to yield purified 3,3-dimethylbutyraldehyde.

15. The method of claim 10, further including a step of distilling after the step of contacting, wherein the distillation isolates said purified 3,3-dimethylbutyraldehyde.

16. The method of claim 10, wherein the first water-immiscible solvent is the same as the second water-immiscible solvent.

17. The method of claim 10, wherein the first water-immiscible solvent is an ether, hydrocarbon, an ester, or a mixture of thereof, and the second water-immiscible solvent is an ether, a hydrocarbon, an ester, or a mixture of thereof.

18. The method of claim 10, wherein said aqueous inorganic base or aqueous inorganic acid is an aqueous solution of hydrochloric acid, sulfuric acid, phosphoric acid, sodium bicarbonate, sodium carbonate, potassium carbonate, potassium bicarbonate, or calcium carbonate.

* * * * *

UNITED STATES PATENT AND TRADEMARK OFFICE
CERTIFICATE OF CORRECTION

PATENT NO. : 5,905,175  
DATED : May 18, 1999  
INVENTOR(S) : ZHI GUO, ET AL.

Page 1 of 2

It is certified that error appears in the above-identified patent and that said Letters Patent is hereby corrected as shown below:

AT [57] ABSTRACT

Line 3, "present" should read --presence--.

COLUMN 1

Line 22, "American of" should read --of American--.

COLUMN 3

Line 1, "in" should read --in- -- and  
    Line 54, "ration" should read --ratio--.

COLUMN 4

Line 48, "the" (second occurrence) should be deleted.

COLUMN 5

Line 55, "1chloro-" should read --1-chloro--; and  
    Line 65, "zinc iodide" should read --zinc iodide,--.

COLUMN 6

Line 49, "of" should read --of:--.

COLUMN 7

Line 6, "carbonate," (first occurrence) should read --bicarbonate,--; and  
    Line 16, "there." should read --thereof.--.

UNITED STATES PATENT AND TRADEMARK OFFICE
CERTIFICATE OF CORRECTION

PATENT NO.  : 5,905,175
DATED       : May 18, 1999
INVENTOR(S) : ZHI GUO, ET AL.

It is certified that error appears in the above-identified patent and that said Letters Patent is hereby corrected as shown below:

COLUMN 8

Line 21, "carbonate," (second occurrence) should read --bicarbonate,--; and
Line 22, "bicarbonate," should read --carbonate,--.

Signed and Sealed this

Twenty-first Day of December, 1999

Attest:

Attesting Officer

Q. TODD DICKINSON

Acting Commissioner of Patents and Trademarks